US010170205B2

(12) United States Patent
Curd et al.

(10) Patent No.: US 10,170,205 B2
(45) Date of Patent: Jan. 1, 2019

(54) MULTI-DIMENSIONAL SURGICAL SAFETY COUNTERMEASURE SYSTEM

(71) Applicant: Karl Storz Endoscopy-America, Inc., El Segundo, CA (US)

(72) Inventors: Steve Curd, Gilroy, CA (US); Mark Heinemeyer, Westlake Village, CA (US); Victor Culafic, Playa Del Rey, CA (US)

(73) Assignee: Karl Storz Endoscopy-America, Inc., El Segundo, CA (US)

( * ) Notice: Subject to any disclaimer, the term of this patent is extended or adjusted under 35 U.S.C. 154(b) by 27 days.

(21) Appl. No.: 13/949,724

(22) Filed: Jul. 24, 2013

(65) Prior Publication Data

US 2015/0033128 A1 Jan. 29, 2015

(51) Int. Cl.

| G06F 3/00 | (2006.01) |
|---|---|
| G16H 40/40 | (2018.01) |
| G06F 3/16 | (2006.01) |
| G06F 19/00 | (2018.01) |
| A61B 34/00 | (2016.01) |
| G16H 40/20 | (2018.01) |

(52) U.S. Cl.
CPC ............. *G16H 40/40* (2018.01); *A61B 34/25* (2016.02); *G06F 3/167* (2013.01); *G06F 19/3481* (2013.01); *G16H 40/20* (2018.01); *A61B 2034/252* (2016.02); *A61B 2034/254* (2016.02)

(58) Field of Classification Search
CPC ......... G06F 9/54; G06F 3/0484; G06Q 10/10; G06Q 50/22; G06Q 50/24
See application file for complete search history.

(56) References Cited

U.S. PATENT DOCUMENTS

| 5,802,542 | A | 9/1998 | Coiera et al. |
|---|---|---|---|
| 6,171,112 | B1 * | 1/2001 | Clark ................. G06Q 50/22 |
| | | | 434/322 |
| 7,920,162 | B2 | 4/2011 | Masini et al. |
| 8,160,896 | B2 | 4/2012 | Klass et al. |
| 8,279,586 | B2 | 10/2012 | Fidacaro et al. |
| 8,308,640 | B2 | 11/2012 | Baldus et al. |
| 8,313,432 | B2 | 11/2012 | Chiu et al. |
| 8,313,433 | B2 | 11/2012 | Cohen et al. |
| 8,326,651 | B2 | 12/2012 | McLaren et al. |

(Continued)

FOREIGN PATENT DOCUMENTS

| EP | 1518501 A2 | 3/2005 |
|---|---|---|
| WO | 03091823 A2 | 11/2003 |

(Continued)

OTHER PUBLICATIONS

European Search Report Application No. 14 17 8284 Completed: Apr. 1, 2015; dated Apr. 9, 2015 11 pages.

(Continued)

*Primary Examiner* — Linh K Pham
(74) *Attorney, Agent, or Firm* — Whitmyer IP Group LLC

(57) ABSTRACT

A multi-dimensional surgical safety countermeasure system and method for using automated checklists to provide information to surgical staff in a surgical procedure. The system and method involve using checklists and receiving commands through the prompts of the checklists to update the information displayed on the display to guide the performance of a medical procedure.

21 Claims, 16 Drawing Sheets

(56) References Cited

U.S. PATENT DOCUMENTS

| | | |
|---|---|---|
| 8,344,847 B2 | 1/2013 | Moberg et al. |
| 8,353,827 B2 | 1/2013 | Brown |
| 8,360,975 B1 | 1/2013 | Schwieterman et al. |
| 8,374,889 B2 | 2/2013 | Arthur |
| 2002/0184002 A1* | 12/2002 | Galli .................................. 704/7 |
| 2003/0204411 A1 | 10/2003 | Beyersdorf |
| 2004/0044546 A1* | 3/2004 | Moore ................................ 705/2 |
| 2004/0049234 A1* | 3/2004 | Morgan et al. .................... 607/5 |
| 2005/0128184 A1* | 6/2005 | McGreevy ......... A61B 18/1206 |
| | | 345/156 |
| 2005/0278197 A1* | 12/2005 | Podczerwinski ... G06F 21/6245 |
| | | 705/3 |
| 2006/0078860 A1* | 4/2006 | Towliat .................. G09B 19/00 |
| | | 434/262 |
| 2006/0138211 A1* | 6/2006 | Lubow ................... G06K 17/00 |
| | | 235/375 |
| 2006/0206011 A1 | 9/2006 | Higgins et al. |
| 2007/0136097 A1 | 6/2007 | Demers et al. |
| 2007/0192133 A1* | 8/2007 | Morgan ................ G06F 19/321 |
| | | 705/2 |
| 2007/0255584 A1* | 11/2007 | Pavlatos et al. .................... 705/2 |
| 2007/0260126 A1 | 11/2007 | Haumann et al. |
| 2009/0018864 A1* | 1/2009 | Gecelter ................ G06Q 50/22 |
| | | 705/2 |
| 2009/0177477 A1 | 7/2009 | Nenov et al. |
| 2009/0216556 A1 | 8/2009 | Martin et al. |
| 2009/0217194 A1 | 8/2009 | Martin et al. |
| 2010/0082368 A1* | 4/2010 | Gecelter ................ A61B 5/411 |
| | | 705/3 |
| 2011/0037840 A1 | 2/2011 | Hiltl et al. |
| 2011/0054944 A1* | 3/2011 | Sandberg .............. G06F 19/322 |
| | | 705/3 |
| 2011/0238431 A1 | 9/2011 | Cionni et al. |
| 2011/0268716 A1 | 11/2011 | Zheng |
| 2012/0323597 A1 | 12/2012 | Woolford |
| 2013/0046543 A1 | 2/2013 | Kitchens et al. |
| 2013/0285947 A1* | 10/2013 | Hunter ................... G09G 5/003 |
| | | 345/173 |
| 2014/0006943 A1* | 1/2014 | Robbins et al. ............... 715/273 |
| 2014/0276056 A1* | 9/2014 | Ohta ...................... A61B 6/465 |
| | | 600/440 |

FOREIGN PATENT DOCUMENTS

| | | |
|---|---|---|
| WO | 2007017642 A1 | 2/2007 |
| WO | 2012174539 A1 | 12/2012 |

OTHER PUBLICATIONS

Extended European Search Report Application No. 15197852.5 dated Apr. 29, 2016; Completed: Apr. 19, 2016 9 Pages.
European Office Action Application No. 14178284.7 dated Sep. 6, 2017 8 Pages.
European Office Action Application No. 15197852.5 dated Apr. 5, 2018 7 Pages.

* cited by examiner

SURGICAL SAFETY CHECKLIST (FIRST EDITION)

World Health Organization

Before induction of anaesthesia >>>>>>>>>>Before skin incision >>>>>>>>>>>>>> Before patient leaves operating room

| SIGN IN | TIME OUT | SIGN OUT |
|---|---|---|
| ☐ PATIENT HAS CONFIRMED<br>- IDENTITY<br>- SITE<br>- PROCEDURE<br>- CONSENT | ☐ CONFIRM ALL TEAM MEMBERS HAVE INTRODUCED THEMSELVES BY NAME AND ROLE | ☐ NURSE VERBALLY CONFIRMS WITH THE TEAM: |
| ☐ SITE MARKED/NOT APPLICABLE | ☐ SURGEON, ANAESTHESIA PROFESSIONAL AND NURSE VERBALLY CONFIRM<br>- PATIENT<br>- SITE<br>- PROCEDURE | ☐ THE NAME OF THE PROCEDURE RECORDED<br>☐ THAT INSTRUMENT, SPONGE AND NEEDLE COUNTS ARE CORRECT (OR NOT APPLICABLE) |
| ☐ ANAESTHESIA SAFETY CHECK COMPLETED | ANTICIPATED CRITICAL EVENTS | ☐ HOW THE SPECIMEN IS LABELED (INCLUDING PATIENT NAME) |
| ☐ PULSE OXIMETER ON PATIENT AND FUNCTIONING | ☐ SURGEON REVIEWS: WHAT ARE THE CRITICAL OR UNEXPECTED STEPS, OPERATIVE DURATION, ANTICIPATED BLOOD LOSS? | ☐ WHETHER THERE ARE ANY EQUIPMENT PROBLEMS TO BE ADDRESSED |
| DOES PATIENT HAVE A: | ☐ ANESTHESIA TEAM REVIEWS: ARE THERE ANY PATIENT-SPECIFIC CONCERNS? | ☐ SURGEON, ANAESTHESIA PROFESSIONAL AND NURSE REVIEW THE KEY CONCERNS FOR RECOVERY AND MANAGEMENT OF THIS PATIENT |
| KNOWN ALLERGY?<br>☐ NO<br>☐ YES | ☐ NURSING TEAM REVIEWS: HAS STERILITY (INCLUDING INDICATOR RESULTS) BEEN CONFIRMED? ARE THERE EQUIPMENT ISSUES OR ANY CONCERNS? | |
| DIFFICULT AIRWAY/ASPIRATION RISK?<br>☐ NO<br>☐ YES, AND EQUIPMENT/ASSISTANCE AVAILABLE | HAS ANTIBIOTIC PROPHYLAXIS BEEN GIVEN WITHIN THE LAST 60 MINUTES?<br>☐ YES<br>☐ NOT APPLICABLE | |
| RISK OF >500ML BLOOD LOSS (7ML/KG IN CHILDREN)?<br>☐ NO<br>☐ YES, AND ADEQUATE INTRAVENOUS ACCESS AND FLUIDS PLANNED | IS ESSENTIAL IMAGING DISPLAYED?<br>☐ YES<br>☐ NOT APPLICABLE | |

THIS CHECKLIST IS NOT INTENDED TO BE COMPREHENSIVE. ADDITIONS AND MODIFICATIONS TO FIT LOCAL PRACTICE ARE ENCOURAGED.

FIG. 16

MULTI-DIMENSIONAL SURGICAL SAFETY COUNTERMEASURE SYSTEM

FIELD OF THE INVENTION

The invention relates to a multi-dimensional surgical safety countermeasure system and method for using automated checklists to provide information to surgical staff in a surgical procedure.

BACKGROUND OF THE INVENTION

Today, it is known that surgeons and surgical staff use checklists when performing a surgical procedure. However, surgical procedures are currently limited to manual and static checklists whereby a surgeon or head of a hospital develops a surgical checklist before beginning the surgery and a hospital surgeon or nurse is responsible for following the checklist during the surgical procedure to ensure that all steps in the surgical procedure are performed on a patient.

This is disadvantageous as patient safety is controlled by a human (i.e. hospital surgeon or nurse tracking the procedure) and steps in the surgical procedure can be missed as human error can occur when coordinating the steps of the surgical procedure. Moreover, the manual and static checklists are unevenly applied in similar surgical procedures, and manual and static checklists are non-engaging to the human staff involved in a surgical procedure.

In addition, the manual and static checklists hinder communication within the operating room as gaps in readily available clinical information exist, and there is an implied hierarchy between, the surgeon, anesthesiologist and nursing staff, which results in poor coordination and efforts through manual checklists.

It is thus desirable to avoid complications in surgical procedures due to manual checklists. Avoiding surgical errors will result in significant improvement in patient satisfaction, referrals, improved perception of clinical administration by operating room ("OR") staff, reduction of unnecessary fees, and costly litigation. It is believed that half of surgical complications today are avoidable through improved communication and by further automating surgical procedures.

Thus, there exists a need to provide a method and system whereby automated checklists are provided to improve surgical procedures. It is desirable to provide a method and system having checklists that are updated based upon clinical information. It is desirable to provide checklists that are dynamic, so that the checklists and steps in the checklists can be updated during a surgical procedure.

SUMMARY OF THE INVENTION

Accordingly, it is an object of the invention to provide a method and system whereby automated checklists are provided to improve surgical procedures. It is another object of the invention to provide a method and system having checklists that are updated based upon clinical information. It is another object of the invention to provide a method and system whereby clinical data is accumulated and an automated checklist is populated based on the clinical data.

These and other objects of the invention are achieved by providing a method for updating information on a display during a medical procedure, the method comprising: collecting data for a patient from at least one database; providing a checklist on a display, the checklist including prompts corresponding to particular stages of the medical procedure; populating the checklist with the data of the patient; receiving commands through the prompts of the checklist; and updating the information displayed on the display based upon the received commands, where the received commands are related to a particular stage of the medical procedure.

In certain embodiments, the method further comprises updating the information displayed on the display based upon the received commands, where the received commands correspond to a complication in the medical procedure. In certain embodiments, the method further comprises updating the checklist based upon the complication in the medical procedure.

In certain embodiments, the method further comprises receiving commands during various stages of the procedure, such that commands are received prior to the beginning of the procedure, during the procedure, and during the ending steps of the procedure to wrap up the procedure.

In certain embodiments, the method further comprises updating the checklist based upon the commands received related to a particular stage of the medical procedure. For example, based upon the commands received, the checklist can be updated and the surgical procedure will change from the surgical procedure initially intended.

In certain embodiments, the method further comprises adjusting the steps of the medical procedure based upon the updated checklist.

In certain embodiments, the commands are received from a member of the surgical team. In certain embodiments, the commands are received from a surgeon located externally to the surgical operating room that is monitoring the surgery electronically or over the web. This allows specialists to monitor the surgery and give advice, while not actually being present and monitoring the surgical procedure.

In certain embodiments, the received commands are transmitted to the database or to a system for the storage of patient information. This allows a database to be built with additional commands, such that commands are stored in a database for referral in a future surgery.

In certain embodiments, the method further comprises updating the physical characteristics of an operating room where the medical procedure takes place. This may involve updating the positioning of the lighting, the positioning of the display monitors and the arrangement of the surgical team members. This may also involve adjusting the height of the surgical table, for example.

In certain embodiments, the color of lighting in the operating room is adjusted based upon a particular stage of the medical procedure. In certain embodiments, the color of the elements of the display monitors are adjusted based upon a particular stage of the medical procedure.

In certain embodiments, the method further comprises providing audio prompts corresponding to a particular stage of the medical procedure. In certain embodiments, the audio prompts include prompts in different languages. In certain embodiments, the audio prompts include prompts for both a male and female voice and wherein the audio prompts can vary in volume intensity based upon the particular stage of the medical procedure.

In certain embodiments, the step of updating the information displayed on the display is automatic. This means that the information displayed on the display is updated automatically without having a user or surgical team member press a button to update the information displayed in the display. Rather the method automatically updates the information based upon the received commands, where the received commands are related to a particular stage of the medical procedure.

In certain embodiments, the checklist is selected from a group of pre-stored checklists based upon the data of the patient. In certain embodiments, the pre-stored checklists are stored in a database or computer system having a plurality of pre-stored checklists for various surgical procedures.

In certain embodiments, the method further comprises providing a rules database, the rules database providing a subset of pre-stored checklists based upon the data of the patient. In certain embodiments, the rules database provides a set of rules that provides certain checklists based upon certain surgical procedures. For example, if the surgical procedure has to do with heart surgery, then only a subset of checklists are allowed for heart surgery. A separate set of checklists are provided for a surgical procedure that is a dermatology procedure, for example.

In certain embodiments, the data is used to pre-populate the checklist prior to initiation of the medical procedure. This means that clinical data related to the patient is merged with the checklist prior to initiation of the medical procedure and the checklist can then be displayed with important clinical data in the steps of the checklist. This way, when a surgeon views the checklist they can also see important clinical information. The clinical information in the checklist is dynamic and can be updated depending upon the progress of the surgical procedure. The clinical information can be updated automatically, this is, if the clinical information displayed in the checklist is a patient's heart rate, it can be updated dynamically based upon the real-time heart rate of the patient during various stages of the medical procedure.

In certain embodiments, the method further comprises tracking the particular stage of the medical procedure via the checklist. In certain embodiments, this involves having the surgeon or nurse view the checklist to determine the particular stage of the medical procedure. In other embodiments, the computer system or display monitor displaying the checklist has processing power that allows the system to track the particular stage of the surgical procedure via the checklist.

Other objects of the invention are achieved by providing a system for updating information on a display in a medical operating room, the system comprising: a display, the display able to display data for a patient from at least one database; a checklist, the checklist displayed on the display, the checklist including prompts corresponding to particular stages of a medical procedure, the checklist being populated with the data of the patient; software executing on a processor, the software tracking the particular stage of the medical procedure via the checklist; and a receiver, the receiver receiving commands through the prompts of the checklist, wherein the software updates the information displayed on the display based upon the commands received related to the particular stage of the medical procedure.

In certain embodiments, the commands received are voice commands. In certain embodiments, the voice commands are due to human responses to electronic prompts or audio prompts.

In certain embodiments, the checklist guides a hospital staff member through the medical procedure based on commands received to checklist steps. In certain embodiments, the medical procedure is a surgical procedure.

In certain embodiments, the display is divided into a first interface and a second interface. In certain embodiments, the checklist is displayed in the first interface, while the clinical data in displayed in the second interface. In certain embodiments, the display changes the data displayed in the second interface. In certain embodiments, the first interface and the second interface are on separate display monitors or computers.

In certain embodiments, the checklist is updated based upon the commands received. In certain embodiments, the commands are received from a surgical team member. In certain embodiments, the commands are received from a person that is remote from the surgical procedure, such that a person that is not on-site performing the surgery can give commands.

In certain embodiments, the system includes software that executes computer programs that run on the processor. In certain embodiments, the software performs various functions to update clinical data stored in the at least one database.

In certain embodiments, the system further comprises lighting in the operating room, wherein the lighting in the operating room is adjusted based upon the particular stage of the medical procedure. In certain embodiments, the lighting in the operating room can dim or increase its intensity based upon the particular stage of the medical procedure. For example, during an intensive step, the lighting can increase to focus the lighting on the patient. During the end of the procedure, the lighting can be dimmed to indicate that the surgical procedure is ending.

In certain embodiments, the colors of display monitors are adjusted based upon the particular stage of the medical procedure. For example the elements of the display monitors can have a green, yellow or red background.

In certain embodiments, the prompts of the checklist include audio prompts corresponding to a particular stage of the medical procedure. For example during the beginning of the procedure, the checklist will give an audio prompt to recite that the surgery is beginning. During a step whereby a patient's chest is to be opened, the checklist will aurally indicate that it is time to open the patient's chest, and to perform various other required steps of the medical procedure.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 16 is an exemplary checklist provided by the World Health Organization ("WHO"), the steps of the exemplar checklist being able to be included in embodiments of the invention.

DETAILED DESCRIPTION OF THE INVENTION

Figure 1:
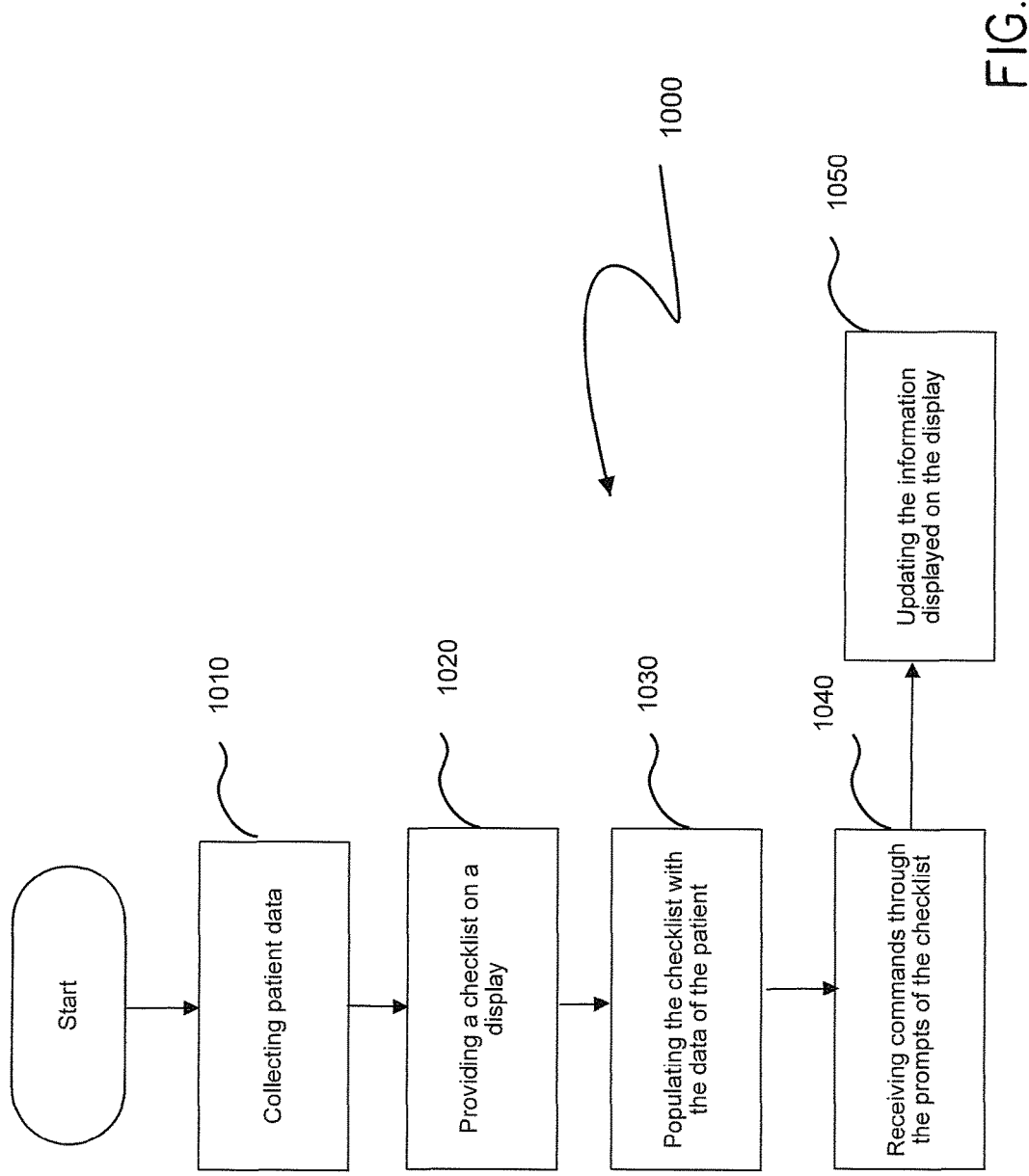
FIG. 1 is a flowchart showing an embodiment of a method of the invention.

In the following description, numerous details are set forth for purpose of explanation. However, one of ordinary skill in the art will realize that the invention may be practiced without the use of these specific details. For instance, the techniques described below are described in a specified order, but other embodiments may change the order of the operations while still embodying the current invention.

Objects of the invention are achieved by providing a method system and device which monitors available clinical patient information originating from various source systems within the care facility (such as Electronic Health Record systems, laboratory systems, radiology systems, vital sign monitoring systems, pharmacy systems, and others), and simultaneously tracks the particular stage of a surgical procedure. The clinical patient information is utilized to automatically adjust clinical information display(s) within the operating room to provide the most essential information necessary to ensure an effective, safe surgical procedure.

In addition, the objects of the invention involve providing customizable checklists to operating room staff at appropriate times, such as prior to initiation of the procedure, following induction of anesthesia, and after completion of the procedure, requiring the human validation of specific factors related to the current stage of the surgical procedure. The responses to these checklists can result in changes to the clinical information displayed, and may optionally be transmitted back to the Electronic Health Record system (or other systems used for the storage of patient information).

In addition, the physical characteristics of the operating room, such as the brightness and color of the ambient lighting, and the content of the available video monitors are automatically adjusted at various stages of the surgical procedure to maximize compliance with processes as defined by clinical studies (such as the W.H.O. Surgical Safety Checklist shown in FIG. 17, and additional factors as defined by the particular surgical facility).

In certain embodiments, aural notification, utilizing unique sounds and human voice prompts, is used to alert all members of the surgical team as to the particular stage of the procedure, and any anomalies which occur that could potentially impact the safety, risk or efficiency of the procedure.

In certain embodiments, the checklist system employs a wide variety of clinical data, patient information, and facility standards and procedures, in order to minimize details that might have been otherwise overlooked.

The result is an integrated, multi-media environment within the operating room which "announces" appropriate steps, requires humans to respond to specific checklists, and adjusts illumination and display of information to reduce the potential for errors caused by information and communication barriers.

This multi-media method and system is far more engaging to the surgical team as by utilizing automated illumination changes and video display changes, the method and system ensures access to critical clinical information by automatically routing the clinical information at the correct time. The method and system also levels information communication by utilizing aural notifications and human voice prompts to the operating room staff.

In the prior art, the content and execution of the checklists have previously been under the discretion of the surgeon. The method and system provided will overcome this disadvantage as facilities will benefit from a more structured and consistent checklist system based on a wide variety of clinical data, patient information, and facility standards and procedures, in order to minimize details that might have been otherwise overlooked. This process will improve surgical procedures, enhance dynamic use of current patient information as well as updates to patient records, and even reduce the possibility of post-operative trauma or infections through improved consistency of healthcare facility surgical standards.

FIG. 1 shows an embodiment of a method of the invention. Here, method 1000 is shown having various steps. The first step of the method shown is collecting patient data 1010. Collecting patient data 1010 can be done by aggregating and accumulating data from at least one patient database. In certain embodiments, the databases can be located in multiple locations and the patient data can be accumulated from various hospital servers and/or computer(s).

The next step in the method involves providing a checklist on a display 1020. Providing a checklist on a display may include providing an automated checklist that is displayed on a dashboard on a display.

In some embodiments, a "dashboard" is a collection of window panes that can be part of a single visual display presentation. A clinical information dashboard of some embodiments is a dashboard where one or more of the window panes displays clinical information (such as vital statistics, lab results, or other clinical information) pertaining to one or more patients. The window panes of a dashboard can be typically collectively viewed in a display, although in some embodiments, the dashboard (and hence some of its window panes) can extend beyond the boundaries of the display. Furthermore, a checklist involves an interface whereby software is executed, the executing software loading a checklist on the dashboard. In certain embodiments, there is a first interface that loads the checklist and a second interface that loads the clinical data.

The checklist can be selected from a database of checklists and can be selected by a surgeon depending on the type of surgical procedure required. For example, if the patient is having heart surgery, then an automated checklist will be selected that is different from a checklist selected for a patient having a dermatology procedure.

The next step of the method involves populating the checklist with the data of the patient 1030. This step involves taking clinical information of a patient and populating the checklist with various information that is critical for the surgical procedure. For example, during a heart surgery, the patient's vitals (blood pressure, sugar level, etc.), are populated into the checklist which is displayed on the display. The type of data that is populated on the checklist that is displayed in the display will vary depending upon the type of surgical procedure required to be performed on a patient.

Furthermore, in certain embodiments, the data that populates the checklist updates the steps in the checklist, so that the steps in the checklist are varied depending upon the progress of the surgical procedure. In this manner, the checklist is dynamic. In certain embodiments, if there are complications in the surgery, the checklist is updatable so that additional steps are provided that account for the surgical complications.

The next steps of the method involve steps taken while performing the medical procedure. During the medical procedure, various commands are received through the prompts of the checklist. For example, in the beginning of the surgical procedure, the checklist may include a step of having each of the team members performing the surgery "sign-in". During the sign-in procedure, the checklist may include an audio prompt whereby surgical team members must state their names. Upon stating their names, a microphone and/or a receiver receives the audio command and converts it to a text string and stores the information in a database. The way such information is stored is described in U.S. patent application Ser. No. 12/247,981 entitled "Voice Controlled Clinical Information Dashboard." The contents of U.S. patent application Ser. No. 12/247,981 is incorporated by reference into this application in its entirety.

During the medical procedure, various commands are received depending upon the type of medical procedure performed. For example, during a heart surgery, the checklist may prompt the surgeons to open up the outer chest of a patient and may guide a surgeon through various steps for opening up the chest of a patient. The checklist may provide various aural and visual cues to surgeons during these steps to help ensure that the surgeon follows all the steps.

The aural and visual cues may involve the system asking a surgeon to view the heart and to provide an answer based upon what the surgeon visually sees. This further reinforces the fact that the surgeon is to perform steps in the medical procedure.

The method also involves updating the information displayed on the display based upon the commands received related to the particular stage of the medical procedure 1050.

Here, based upon the command received by the surgeon or team member, the clinical data displayed on the display is updated. For example, if the surgeon indicates that a patient is bleeding, then the clinical data displayed on the display may include the patient's blood pressure and other factors that may relate to a patient bleeding.

In another example, if the surgeon indicates that he is cutting into a patient's heart, then data such as the patient's blood pressure and heart beat may be displayed in the display.

The clinical data displayed in the display is also related to the particular stage of the medical procedure. Thus, for example, data displayed during the beginning of the medical procedure is different from data displayed during the end of the medical procedure.

For example, during the beginning of a medical procedure, general data is displayed, which is related to the type of medical procedure performed or is related to general information about the patient. As the medical procedure progresses, specific clinical information is displayed, which is directed to the particular stage of the medical procedure, i.e., a patient's blood pressure is displayed when the medical procedure involves heart surgery and the surgeon is cutting into a patient's heart.

In certain embodiments, the checklist is dynamic and the data displayed in the display is dynamically updated based upon complications that occur in the surgery. In certain embodiments, the checklist is updated based upon the clinical data of a patient and based upon parameters during a surgery.

For example, if a surgeon realizes that a complication in a heart surgery occurs, which affects another organ in the body such as the liver, then the checklist is dynamically updated so that a surgeon is taken through the steps to check and operate on the liver, if necessary. In this manner, the checklist is automatically updated and the information displayed on the display is updated based upon the command received related to the complication in the medical procedure.

In another embodiment of the invention, the information displayed on the display is updated based upon the discrete step of the medical or surgical procedure. For example, during heart surgery the data displayed on the display during the step of opening the chest of a patient will be different than the data displayed when the surgeon is operating on the patient's heart. The checklist and computer system processing the checklist understands the particular stage of the medical procedure and updates the clinical information displayed on the display during the particular stage of the medical procedure. The checklist is able to understand the stage of the medical procedure by receiving aural information from surgeons or surgical team members as such team members state that certain portions of the procedure have been completed, thus, updating the checklist.

In certain embodiments, the information may be displayed in a window pane (also referred to as the "view" of a window pane) and may be presented in different forms, including reports, lists, notes, graphs, two-dimensional and three-dimensional images, etc. Each window pane can present one or more views of (1) one or more clinical data items (e.g., a list or graph associated with a vital signal or lab measurement) or (2) established treatment guidelines or protocols (e.g., guidelines from public reference sources or from customized intramural institutional policies regarding particular conditions or measurements).

Figure 2:
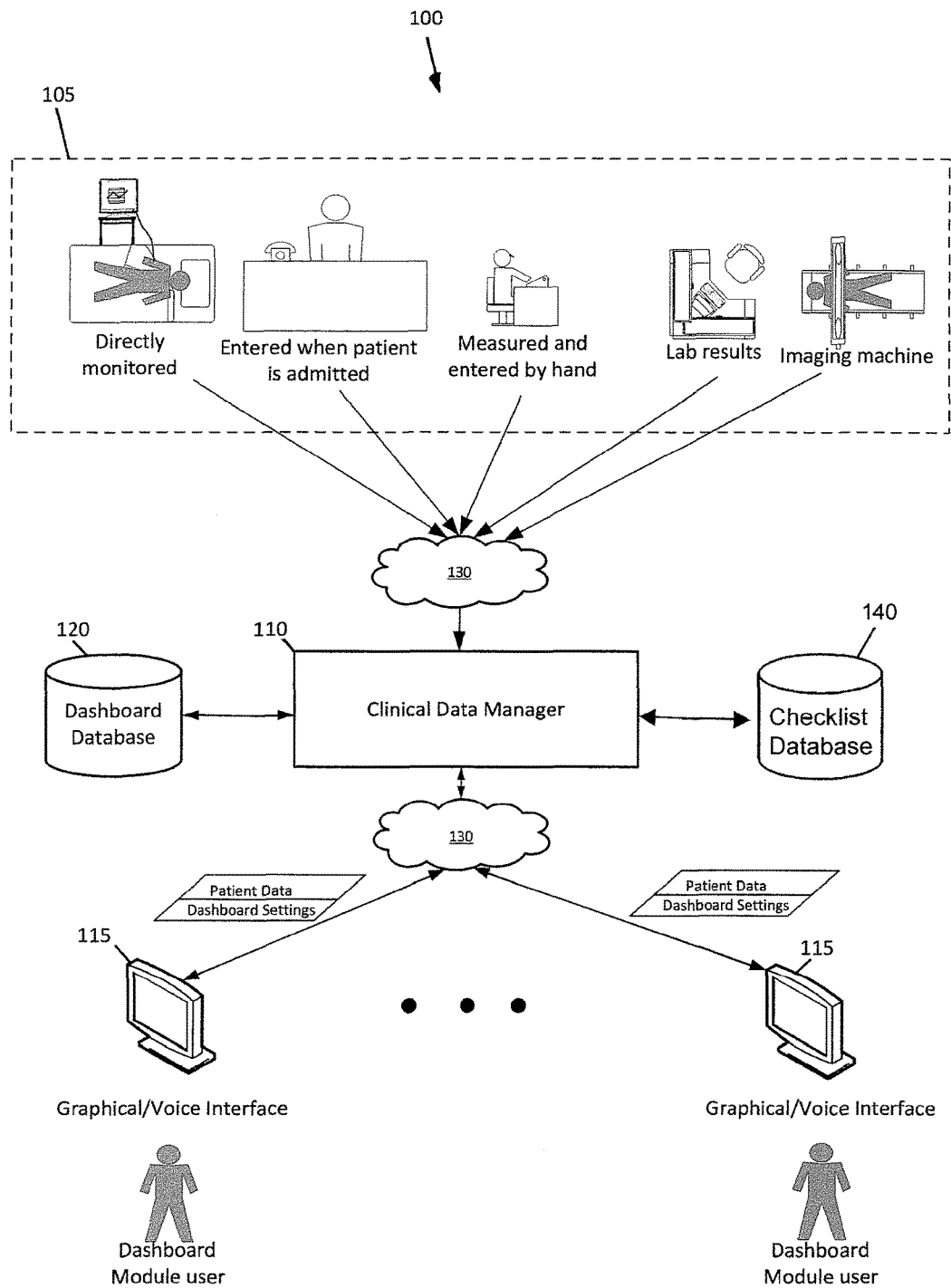
FIG. 2 illustrates a conceptual system architecture of some embodiments of the invention.

FIG. 2 conceptually illustrates system architecture 100 of a clinical information system which uses checklists and dashboards to interactively provide information to medical practitioners. The system architecture 100 includes several clinical data sources 105, a clinical data manager 110, a set of graphical/voice interfaces 115, a dashboard database 120, and a network 130. As shown in FIG. 2, the clinical data manager 110 receives patient data from several disparate patient data sources 105. In some embodiments, the clinical data manager 110 receives data from one or more of these patient data sources 105 through the network 130. The network 130 of some embodiments is a local area network, ("LAN"), a wide area network ("WAN"), a network of networks (e.g., the Internet), or some other network.

Examples of such sources 105 of patient data include direct monitoring (i.e., data collected from machines that are directly connected to a patient), data entered when a patient is admitted, data entered by hand (e.g., by a healthcare provider pursuant to an examination), lab results, and/or imaging machine data. Although only a few examples are mentioned, one of ordinary skill in the art would recognize that other sources of information (not shown) may provide information to the clinical data manager 110.

The clinical data manager 110 collects objective data, such as vitals from monitors monitoring the patients, lab reports, and medical images (e.g., x-rays, Magnetic Resonance Imaging ("MRI"), Computed Tomography ("CT") scans, etc.) as well as subjective data such as physicians' assessments, physicians' diagnoses, or physician treatment plans from the various data sources 105. In some embodiments, the clinical data manager 110 receives information from a dashboard database 120, which may include previously recorded patient data from any source, including any of the abovementioned sources 105. The data collected by the clinical data manager 110 may arrive from one or more locations, such as different labs, different locations within a single hospital, and/or multiple different hospitals. In some embodiments, the relevant data is not only pulled from medical facilities, but also from different servers across the Internet (e.g., library, educational institutions, etc.). Such collection of data from multiple locations is described in more detail in U.S. patent application Ser. No. 12/036,285, entitled "Patient Monitoring," filed Feb. 24, 2008, the contents of which are herein incorporated by reference.

The clinical data manager 110 of some embodiments receives, normalizes, analyzes, and/or aggregates the patient data for the purposes of gathering data about individual patients (as a snapshot of a patient's data or as a record of the data over time), and/or for the purpose of comparing statistics among patients (in some cases including the change, or "delta," in statistics of each patient) for various reasons. For instance, these statistics may be normalized and compared in order to efficiently allocate medical resources.

The clinical data manager 110 of some embodiments reports data, disseminates data, and/or alerts users to data through various clinical information interfaces 115. In some embodiments, this reporting, dissemination, and or alerting is done by transmitting patient data to the interfaces 115 through a network 130 (e.g., the Internet, a LAN, or some other network).

In some embodiments, these interfaces 115 include one or more display devices. The display devices of some embodiments include a single display device, such as a computer monitor, television screen, PDA screen, computer tablet, etc. In some embodiments, an interface 115 includes multiple display devices. In some of these embodiments, an interface 115 includes an array of display interfaces (e.g., a "data wall").

In some embodiments, an interface 115 displays one or more "intelligent" dashboards that display different data, depending on the situation. Such intelligent dashboards are further described in more detail in U.S. patent application Ser. No. 12/036,287, entitled "Intelligent Dashboards," filed Feb. 24, 2008, the contents of which are herein incorporated by reference.

In some embodiments, the interfaces 115 of FIG. 2 display intelligent dashboards with different information from each other depending on different criteria, including the job of the user within the medical system, the particular terminal on which the interfaces 115 are displayed, and/or the momentary needs of the individual user (i.e., healthcare provider) and/or patient. In some embodiments, the intelligent dashboards of the various interfaces 115 display different information depending on where the interface 115 is located. For example, an interface 115 for a user in a cardiac intensive care unit ("ICU") may provide a dashboard with one set of data, while another interface 115 for a user in neurosurgery may provide a dashboard with a different set of data. Moreover, in some embodiments, the interface 115 may provide different information depending on a particular patient's diagnosis or condition. The clinical data manager 110 of some embodiments can also provide the data in real-time to the various interfaces 115.

In some embodiments, the dashboard database 120 stores information relating to the customization of presentation of information through the interfaces 115 based on several factors, including, as mentioned above, (1) the identity of a user of the interface 115 and/or (2) the location of a user of the interface 115. In other words, the dashboard database 120 may store settings for displaying user- and/or location-based customized dashboards. In some embodiments, these settings include a user-customized layout of modalities. The user-customized layout of some embodiments specifies location and/or size of modalities within the dashboard. These customized layouts may be modified, saved, and recalled at a later time in some embodiments.

In some embodiments, the clinical data manager 110 provides these stored settings to an interface 115 upon a request to the clinical data manager 110 by the interface 115 (e.g., when a user logs in to the interface 115). Additionally, a user may make changes to existing settings, or create new settings, at an interface 115. The dashboard database 120 may then store these settings for retrieval at a later time (e.g., when the user logs in to an interface 115 at a subsequent time).

Although FIG. 2 illustrates the interfaces 115 as sending and receiving dashboard settings from the clinical data manager 110, in some embodiments, one or more of the interfaces 115 sends and receives dashboard settings directly to and from the dashboard database 120. In some embodiments, the dashboard database 120 and the clinical data manager 110 physically reside on the same hardware (e.g., a single computer). In other embodiments, the dashboard database 120 and the clinical data manager 110 reside on separate hardware (e.g., two or more different computers). The dashboard database 120 and the clinical data manager 110 of some embodiments are communicatively coupled through a network (not shown), such as a LAN, a network of networks (e.g., the Internet), or some other network.

Some embodiments provide several manual tools for that allow user interaction with the interfaces 115 in order to access desired information. These manual tools may include traditional input devices, such as mice, keyboards, touch screens, trackpads, etc. In some embodiments, one or more of the interfaces 115 includes a voice-control input component that allows a user of the interface 115 to interact with the dashboard through voice commands. Thus, one or more of the interfaces 115 of some embodiments provide (1) a visual component (i.e., a graphical user interface, or "GUI") that interactively displays patient information and (2) an input component, which includes voice command functionality of some embodiments for interacting with the GUI.

Such user control is correlated to checklists that are stored in checklist database 140. The clinical data manager 110 interacts with a checklist database 140, such that various checklists are able to be uploaded onto the graphical/voice interface 115.

In certain embodiments, the checklists stored in the checklist database interact with the dashboards stored in the dashboard database 120, so that various dashboards that display clinical data are shown in the display based upon the particular stages of the medical procedure and based upon command received.

In certain embodiments, the commands are received by a microphone or receiver. In certain embodiments, the commands received are processed by a processor stored in a computer.

Figure 3:
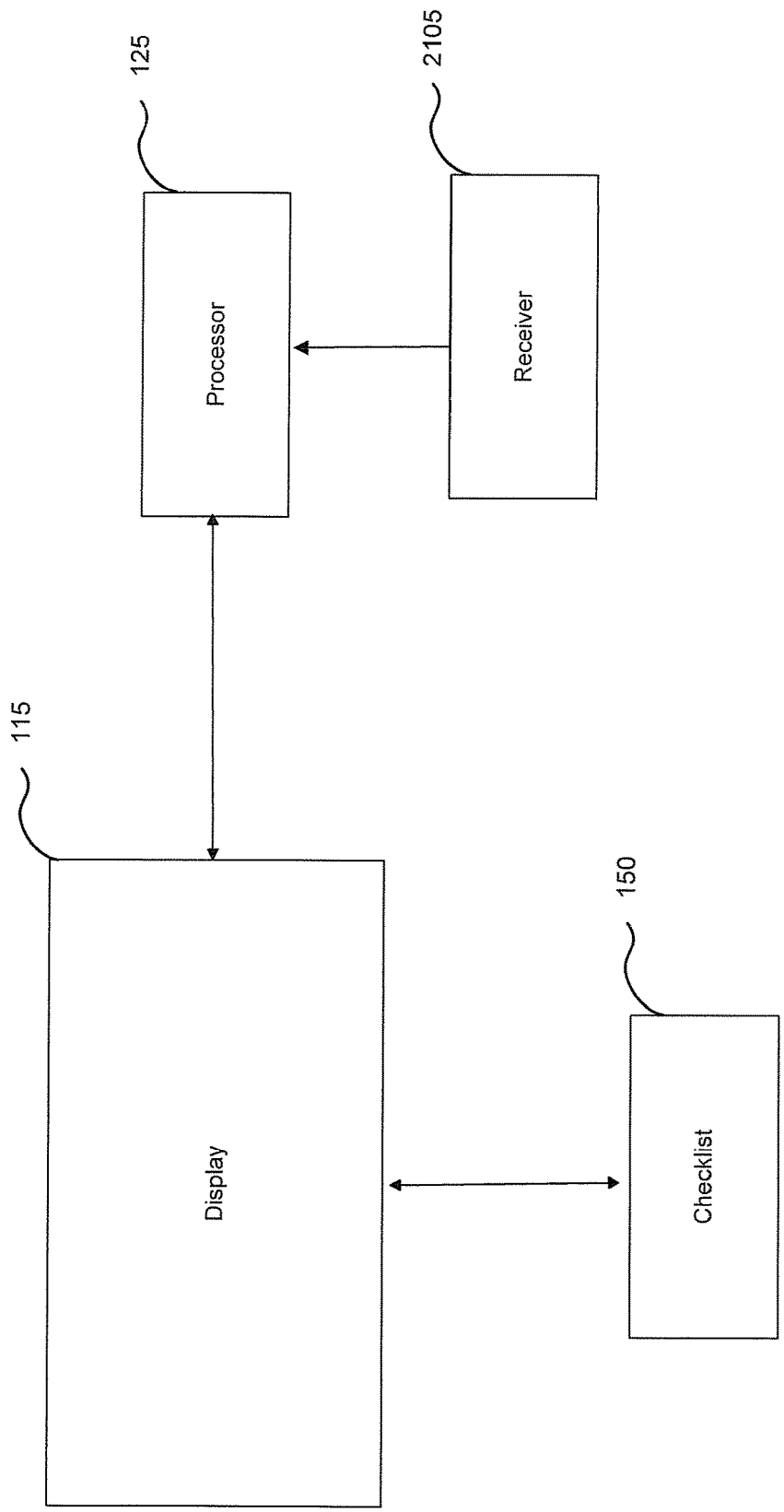
FIG. 3 is a block diagram showing elements of the invention.

As shown in FIG. 3, a display 115 (graphical/voice interface) is shown as well as a processor 125 and receiver 2105. When a surgical team member gives a command, the receiver 2105 (a microphone for example) receives the emitted command and the command is transmitted to a processor 125. The processor then executes a computer program and updates the information displayed on the display based upon the commands received related to the particular stage of the medical or surgical procedure.

In certain embodiments, software that processes the command takes the command and compares it against a database that includes various commands that are associated with functions to update the checklist. Certain commands will cause the checklist to be updated and to affect the steps of the surgical procedure.

In certain embodiments, the commands cause the dashboard and the information displayed to be updated. Furthermore, the commands cause the checklist displayed on the display to be updated based upon the clinical information. In certain embodiments, the automated checklists check for changes in the clinical data. If there are changes, then the checklists alert members of the team. The checklists take the direction of the surgery away from the lead surgeon and give it to an automated computer/processor that is dynamic.

In certain embodiments, characteristics of the operating room are adjusted based upon the checklists. Once a checklist is selected then, the lighting in the operating room has various color settings related to issues of the safety of the environment. In certain stages of the medical procedure, lighting in the operating room is adjusted based upon the checklists. In certain embodiments, the type of display can be adjusted based upon the checklists.

Figure 4:
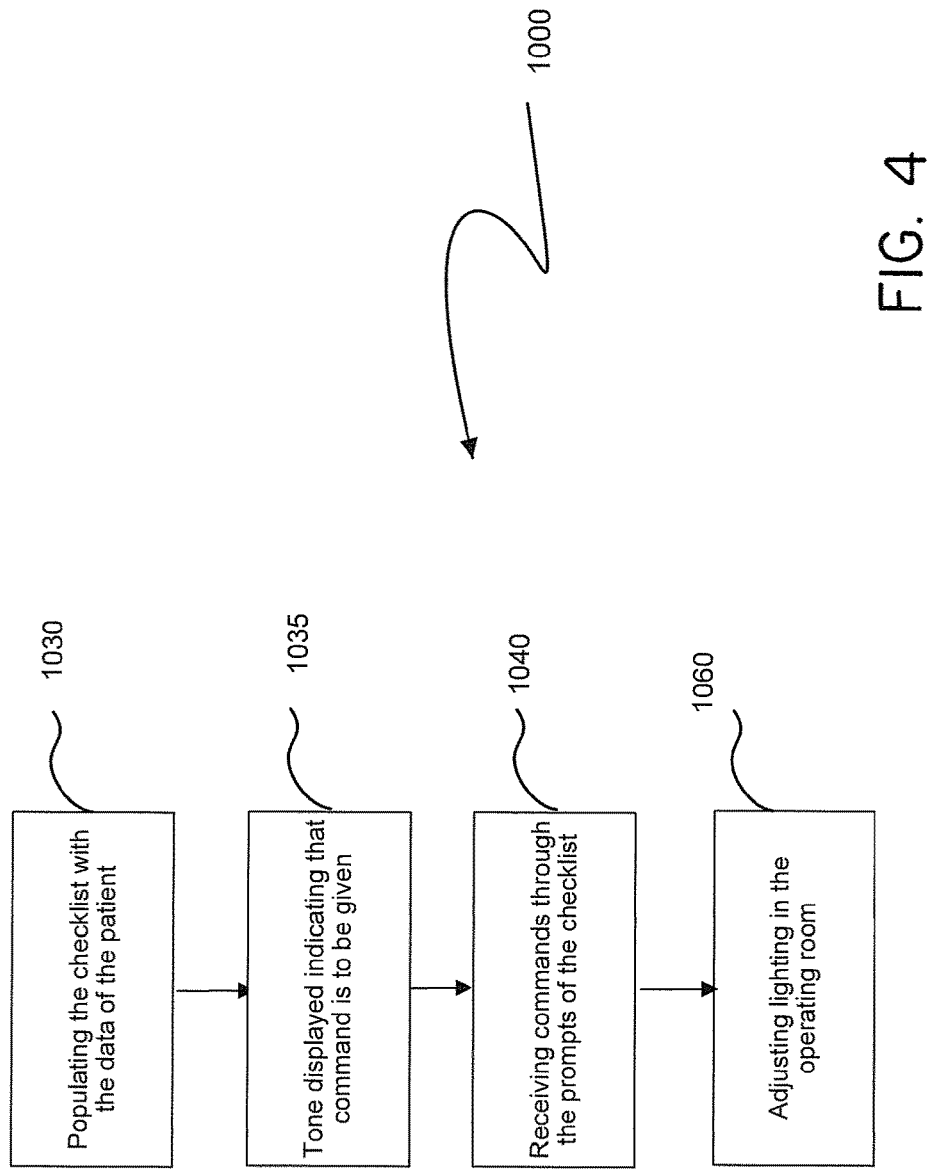
FIG. 4 is a flowchart showing various steps of an embodiment of FIG. 1.

Shown in FIG. 4, after the information displayed on the display is updated 1050, the step of adjusting lighting in the operating room 1060 can occur. The lighting may be adjusted to have different colors for different steps of the surgical procedure. In other embodiments, the lighting may be adjusted, such that if there is a problem in the surgical procedure or if there is a step in the surgical procedure that must be done more carefully, the lighting is adjusted and/or alerts may be given.

In certain embodiments, the checklists have different color displays. For example during sign-in the checklist could be red, during patient anesthesia the checklist could be yellow and then green during a surgical procedure. If something goes wrong, then the checklist could revert back to yellow or even red.

In certain embodiments, the checklist prompts use a different voice for different portions of the surgical procedure. The checklist prompts may use the voices of the surgical team members. In certain embodiments, a certain voice may be used where there are complications in the procedure. In certain embodiments, a male voice is used and in other embodiments a female voice is used. In certain embodiments, both a male and a female voice are used at different portions of the procedure to keep the surgical staff concentrated.

In certain embodiments, there are voices in different languages and more than one language. In certain embodiments, there are tones that are played to precede different notifications and to precede different steps in the medical procedure.

FIGS. 5-13 show an operating room having displays that use checklists. These figures are shown in color, so that various embodiments of the invention are shown.

Figure 5:
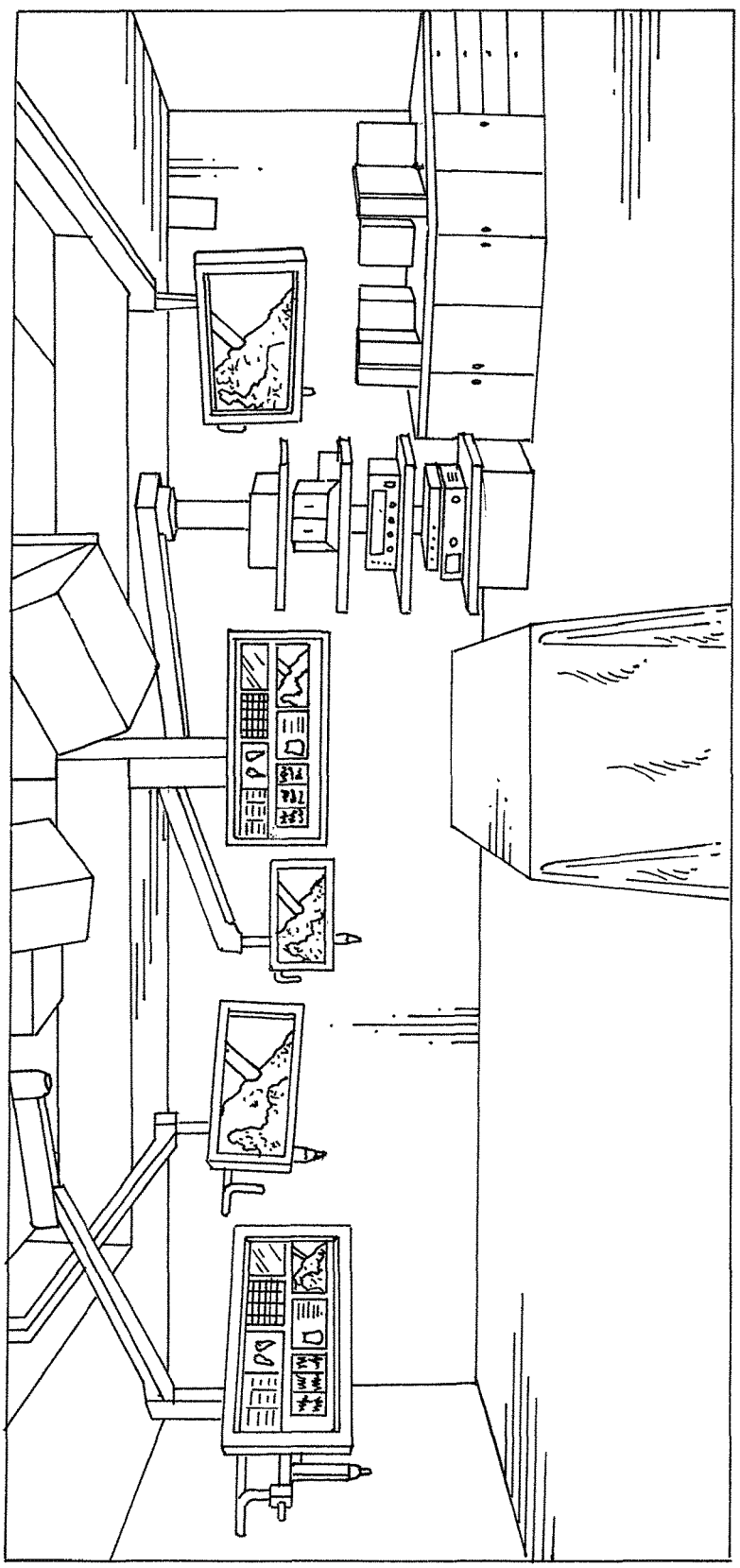
FIG. 5-13 are various color photographs of updates to clinical data and display monitors during a surgical procedure.

FIG. 5 shows a surgical operating room environment having various display monitors showing clinical data of a surgical procedure. The clinical data shown is in the form of graphs, lists, tables and other types of data that assist surgeons to perform a surgical procedure.

Figure 6:
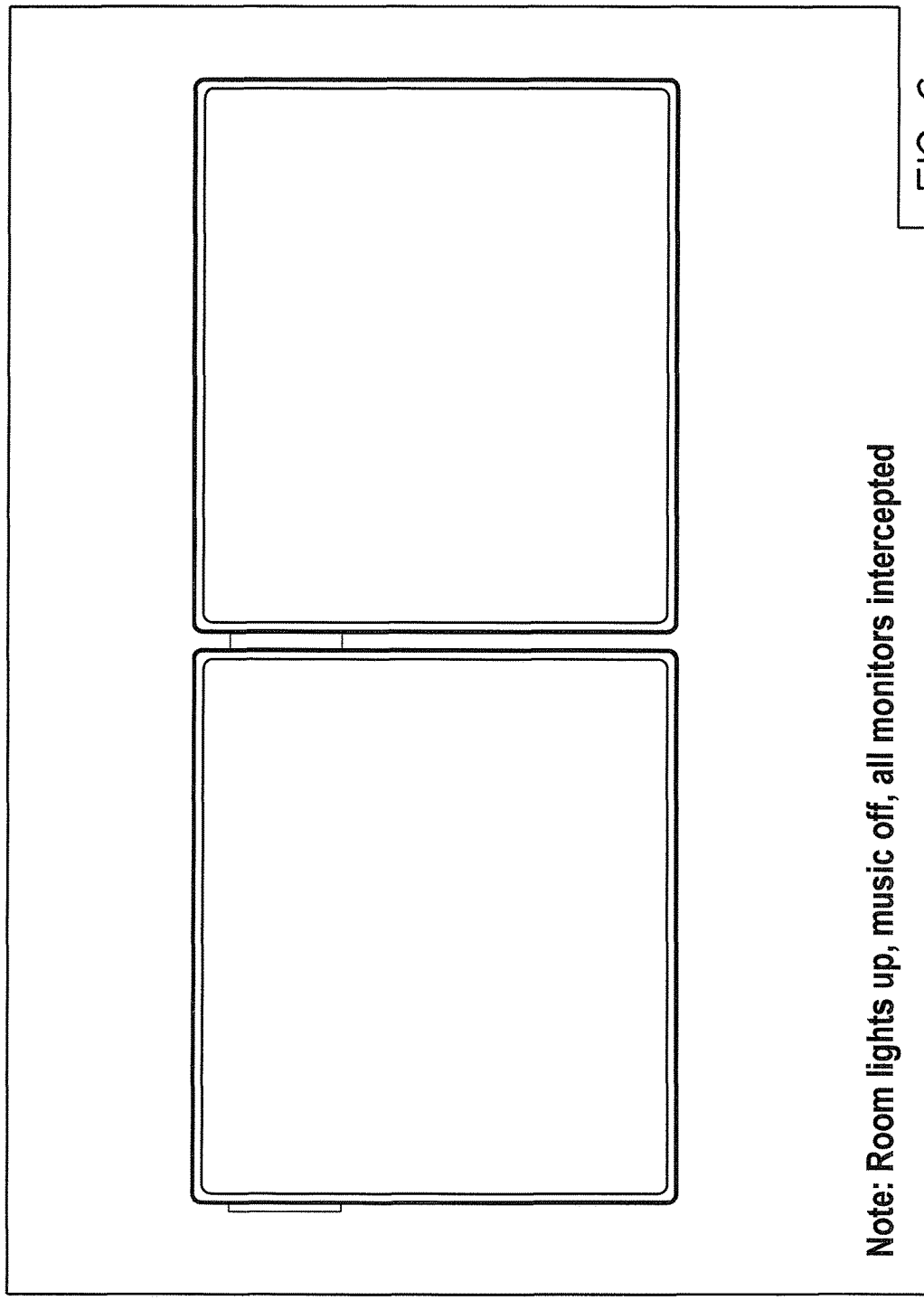

FIG. 6 shows a close up view of two display monitors. The display monitors are shown with a red border indicating that the room lights up, music off, all monitors intercepted and that the surgical procedure has not yet begun.

Figure 7:
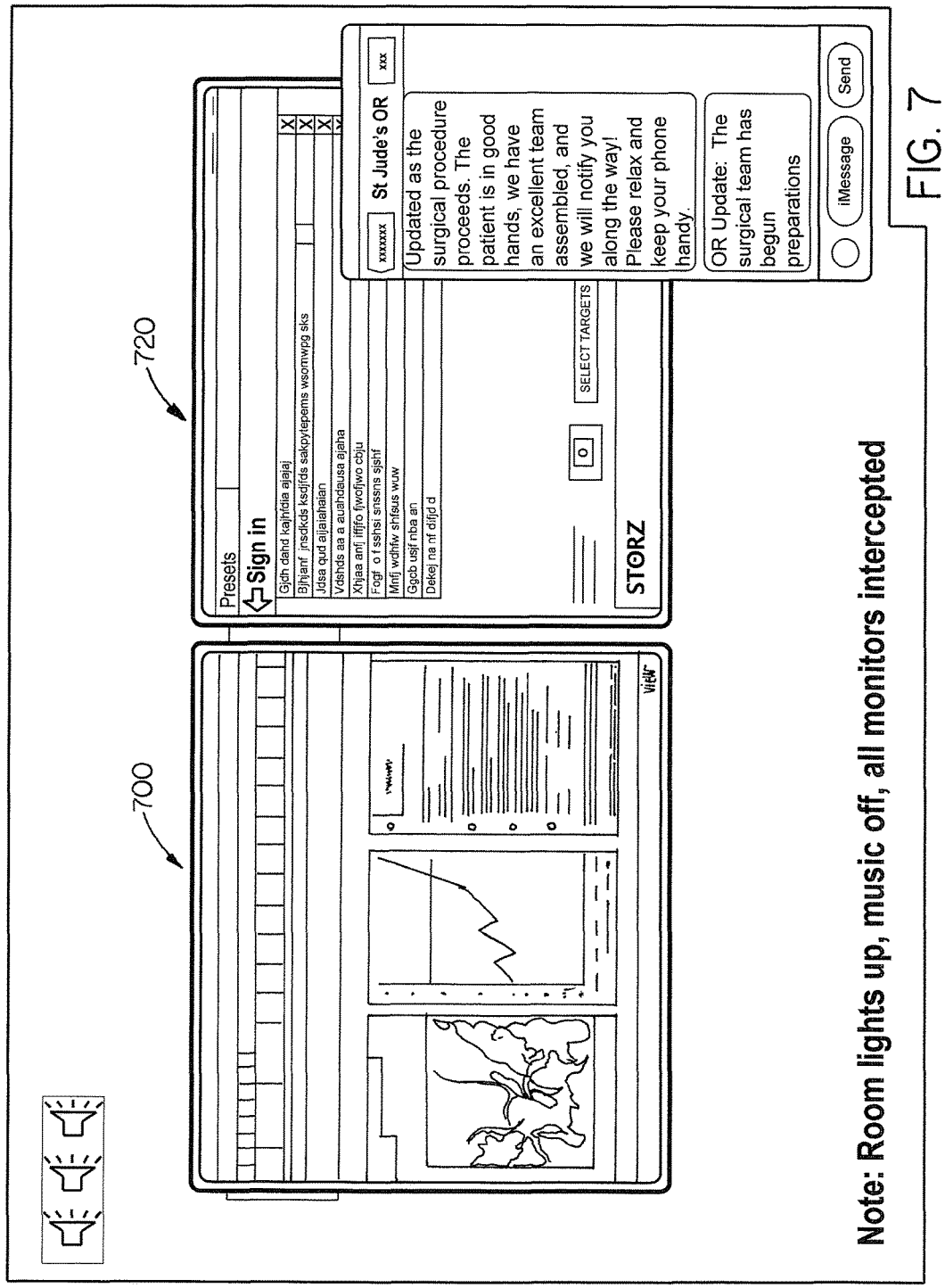

FIG. 7 shows the two displays monitors 700 and 720. Display monitor 700 displays clinical data in various charts and tables and display monitor 720 shows an electronic checklist, the electronic checklist having various steps checked off indicating that such steps have been performed, while also having steps checked off in the no box indicating that the steps have not been performed.

FIG. 7 also shows a smart phone whereby various updates are transmitted to the phone as the surgical procedure progresses. In certain embodiments, the checklist is linked to a smart phone as the checklist causes software executing on the controller to send updates to the smart phone. Such updates are sent via text message, SMS, imessage and various other types of instant messenging services. Such smart phones may be given to members of a patient's family such that a patient's family is automatically updated as the medical procedure progresses.

Furthermore, during the surgical steps associated with FIG. 7, audio is played in the surgical environment as indicated by three volume icons in FIG. 7. The level of audio can vary depending on the step and the complexity of step of the surgical procedure. Furthermore, the audio is tied to the checklists as various steps in the checklist are provided to the surgical staff in the form of audio prompts.

Figure 8:
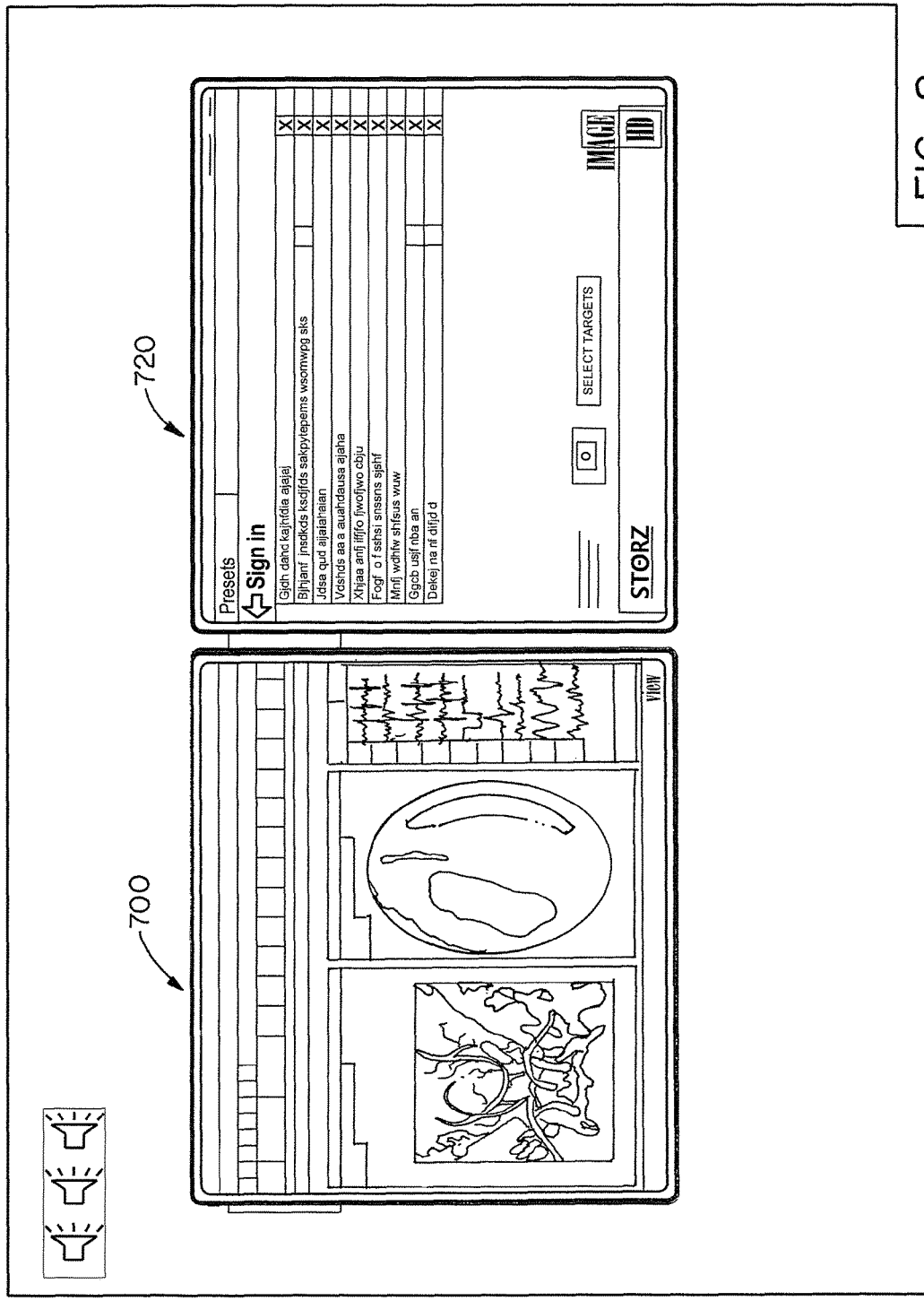

FIG. 8 shows display monitor 700 and display monitor 720 as the surgery progresses. Here, various steps are taken whereby the clinical information displayed on display monitor 700 changes as the surgery progresses. Furthermore, the background of the display monitors changes to yellow color. In certain embodiments, this indicates that the surgery is in a different portion of the procedure. In certain embodiments, the yellow background may indicate that a surgeon should be more careful during the particular step of the surgery.

Furthermore, in FIG. 8, display monitor 720 has various steps checked off in the checklist. During the surgical steps associated with FIG. 8, audio is played in the surgical environment as indicated by three volume icons in FIG. 8.

Figure 9:
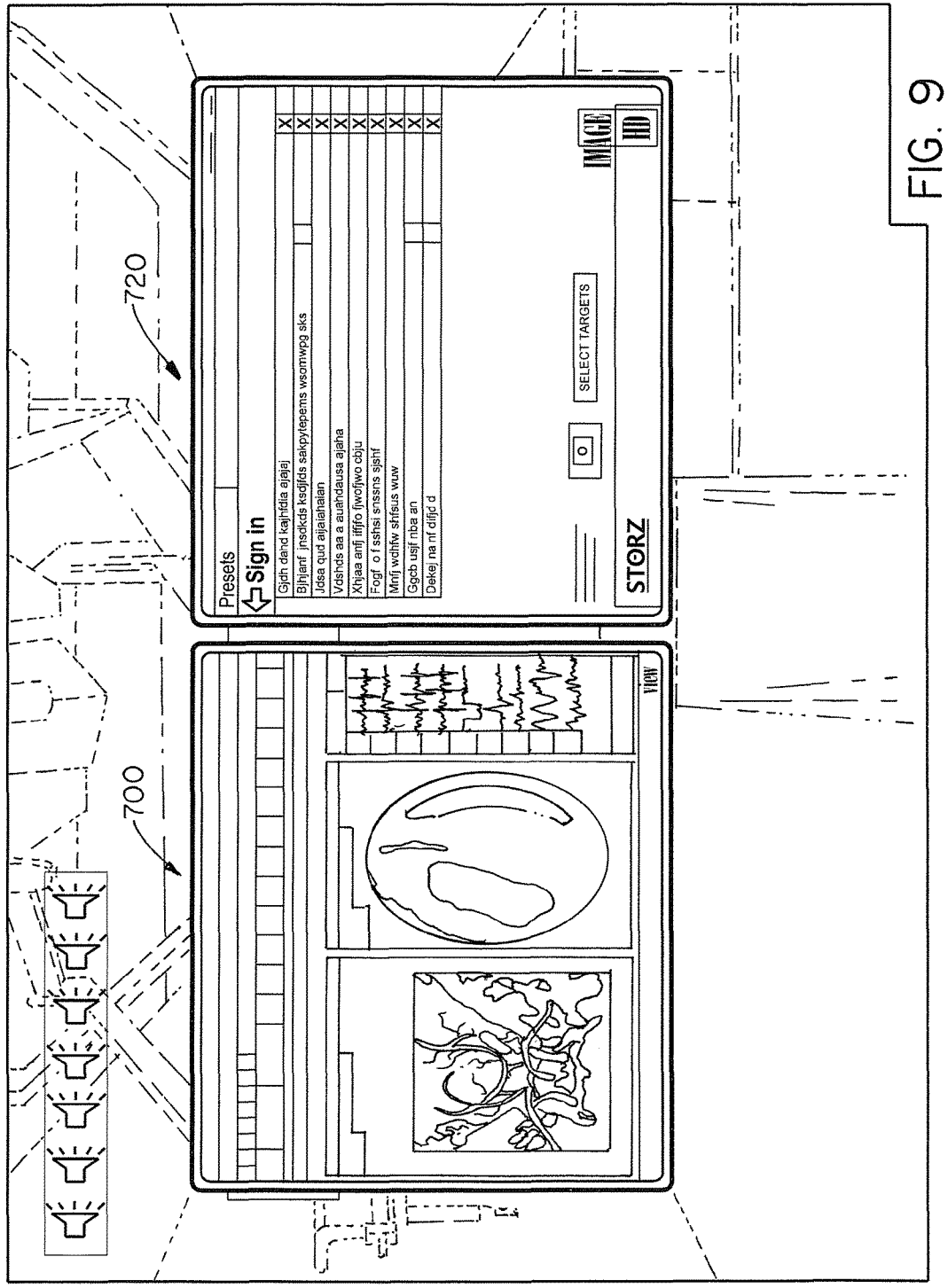

FIG. 9 shows display monitor 700 and display monitor 720 as shown in FIG. 8. However, during the surgical steps performed when the clinical data displayed in FIG. 9 is shown, the volume level of the audio increases from three volume level icons in FIG. 8 to seven volume level icons shown in FIG. 9.

Figure 10:
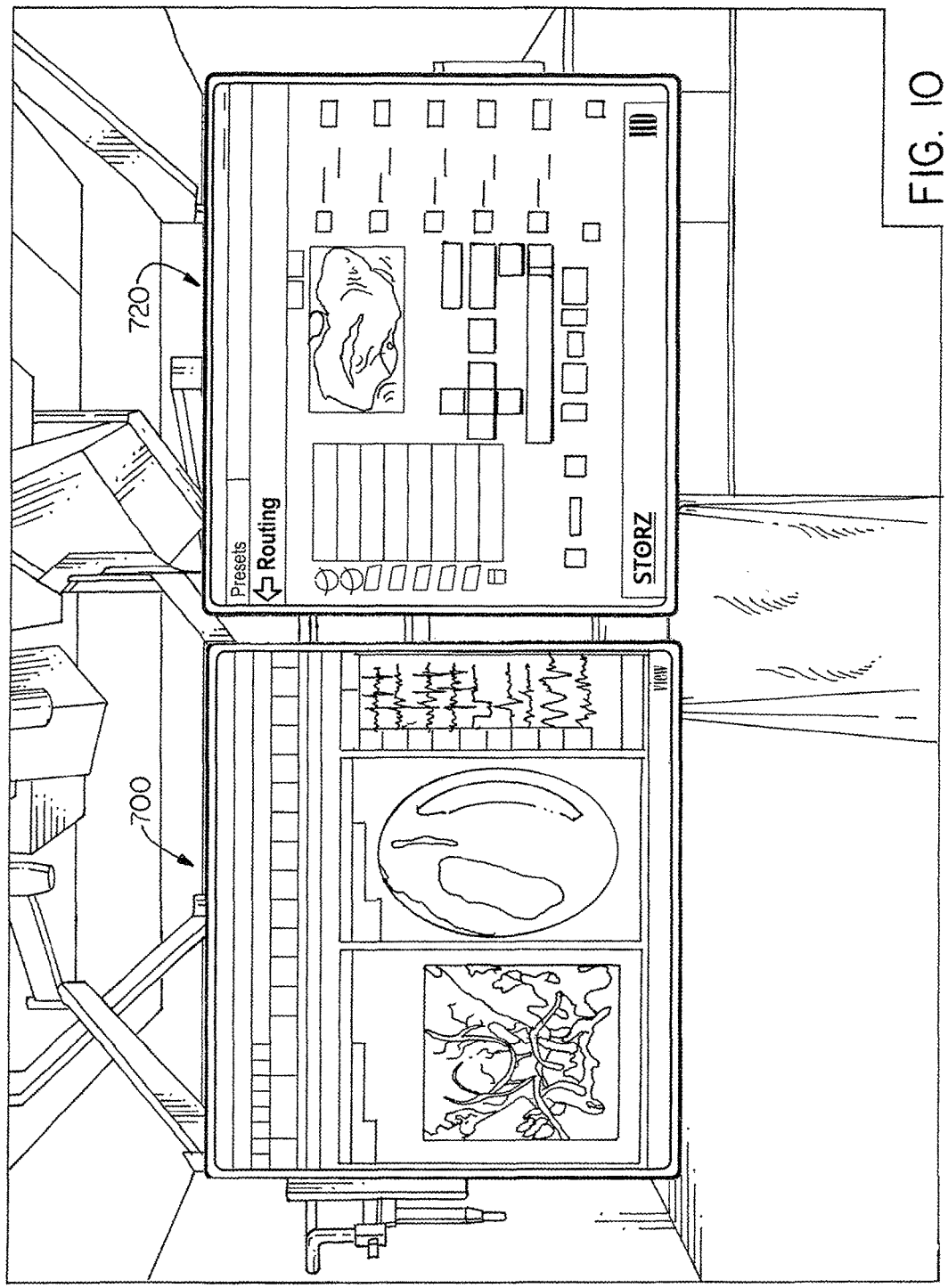

FIG. 10 shows display monitors 700 and 720 with a green background, rather than a yellow background. Here, the display monitor 720 has clinical data replacing or overlaying the checklist in the display. The clinical data shown in display monitor 720 is a blown up view of the surgical images shown in display monitor 700, with various toggling options to focus on the images shown in the display.

Figure 11:
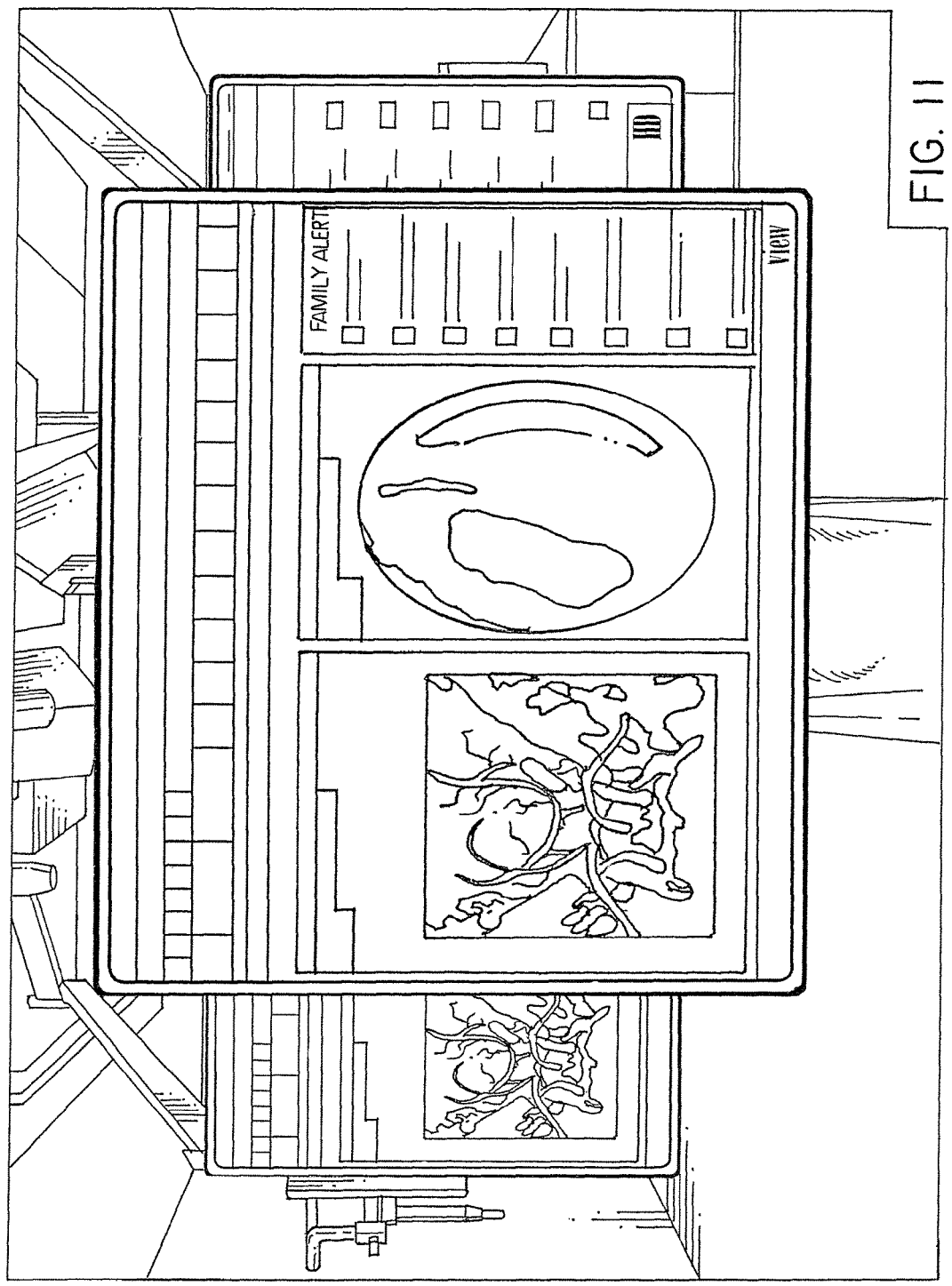

FIG. 11 shows a blown-up view of display monitor 700 shown in FIG. 10. Here, the monitor 700 is shown having a checklist for various "family alerts" whereby at various portions of the surgical procedure, the patient's family is automatically updated with updates sent to their phone of how the surgery is progressing. The surgical team members can inform the system via aural commands that certain portions of the surgery have been completed and the system sends the updates to the smartphone given to members of the patient's family.

Figure 12:
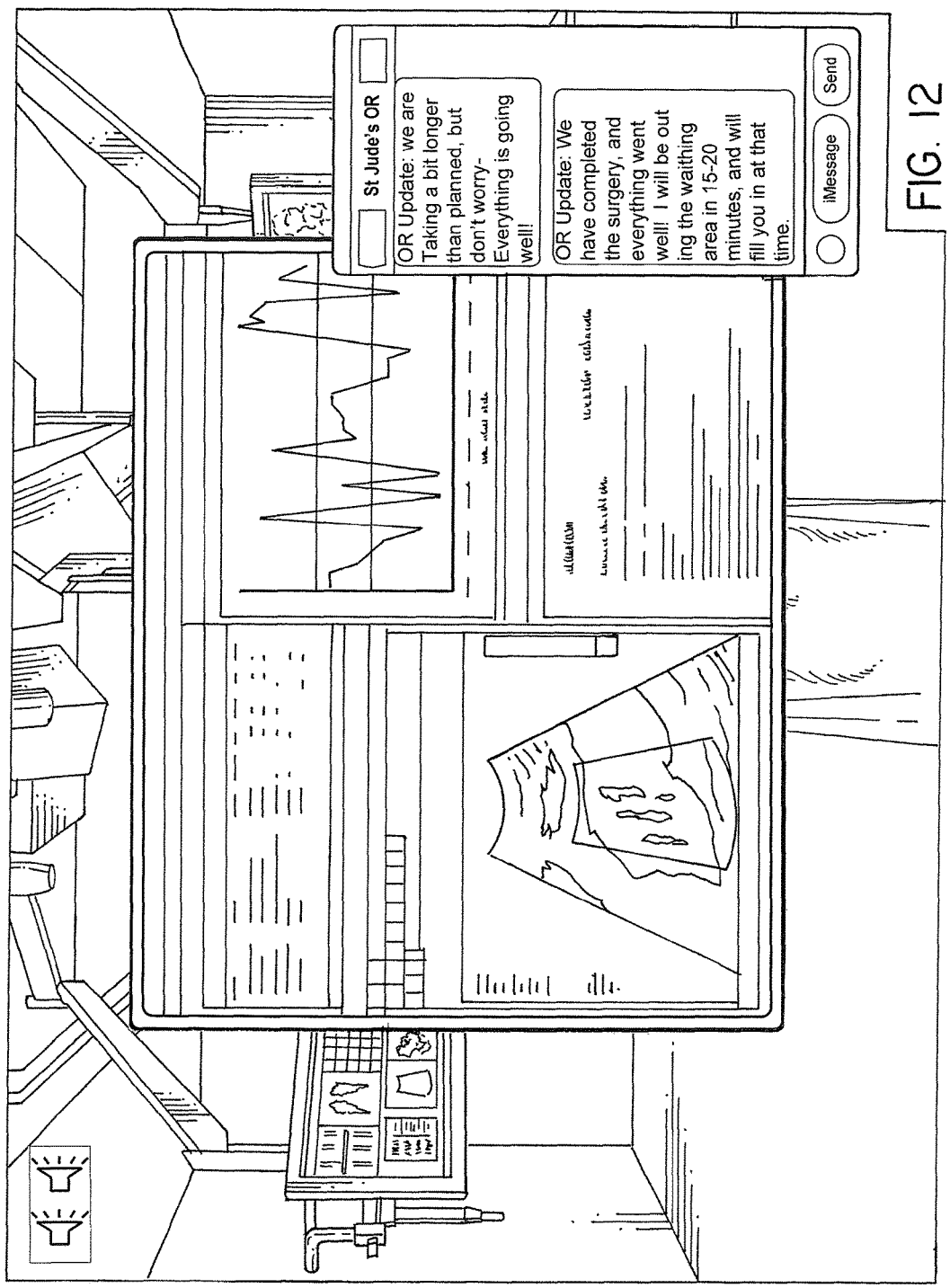

FIG. 12 shows a close-up view of a display monitor whereby various clinical data is shown in windows in the display. Here, patient data is shown that is updated depending upon the step of the surgical procedure. The background of the display monitor shown in FIG. 12 is yellow. Furthermore, FIG. 12 shows a smart phone whereby the patient's family receives information that the surgery is completed and the surgeon will update the family after the completion of the surgical procedure.

Figure 13:
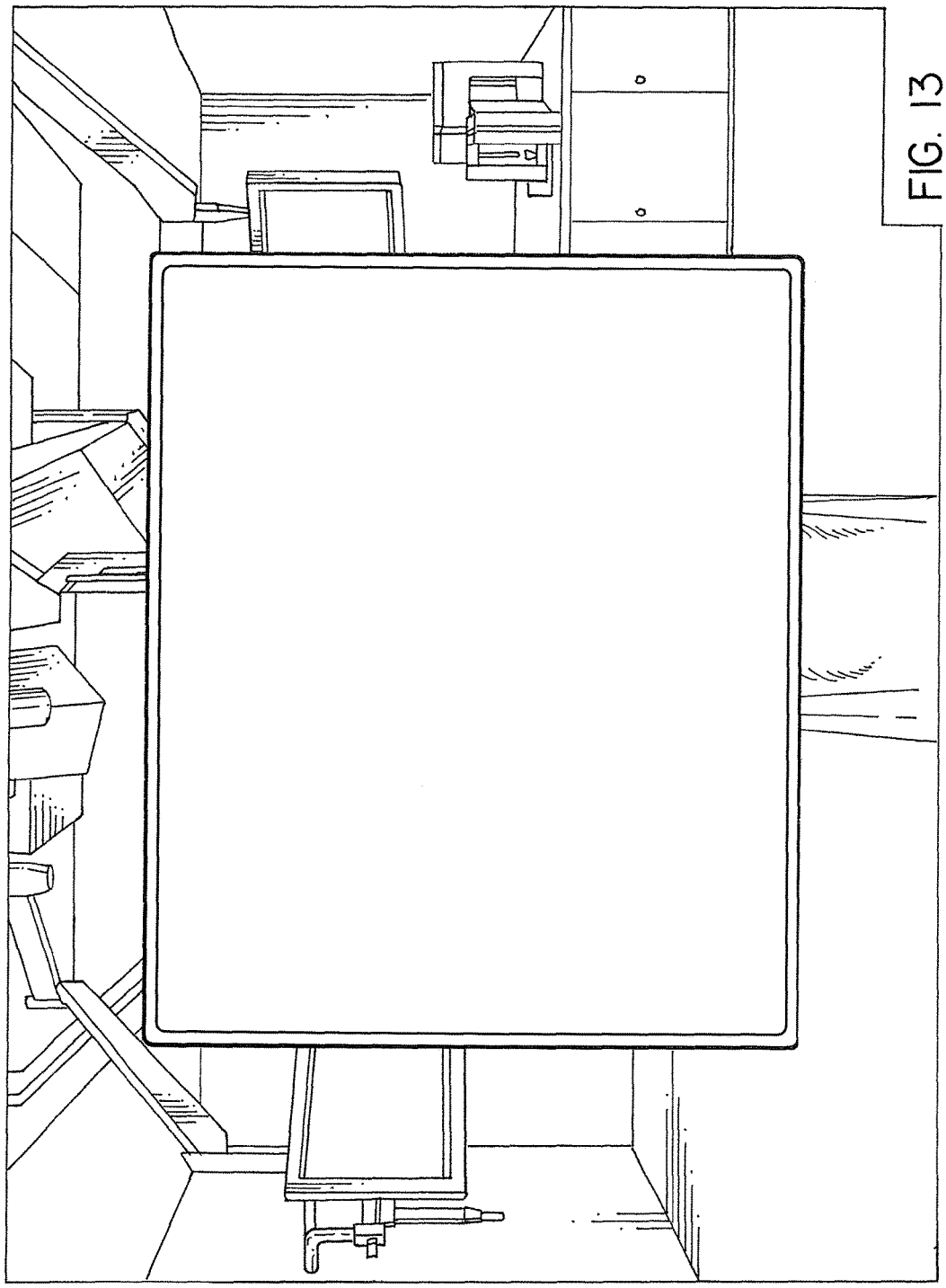

FIG. 13 shows a close of view of a display monitor where the surgery is completed and no clinical data is shown in the display. The background of the display monitor when the surgery has completed is red.

Figure 14:
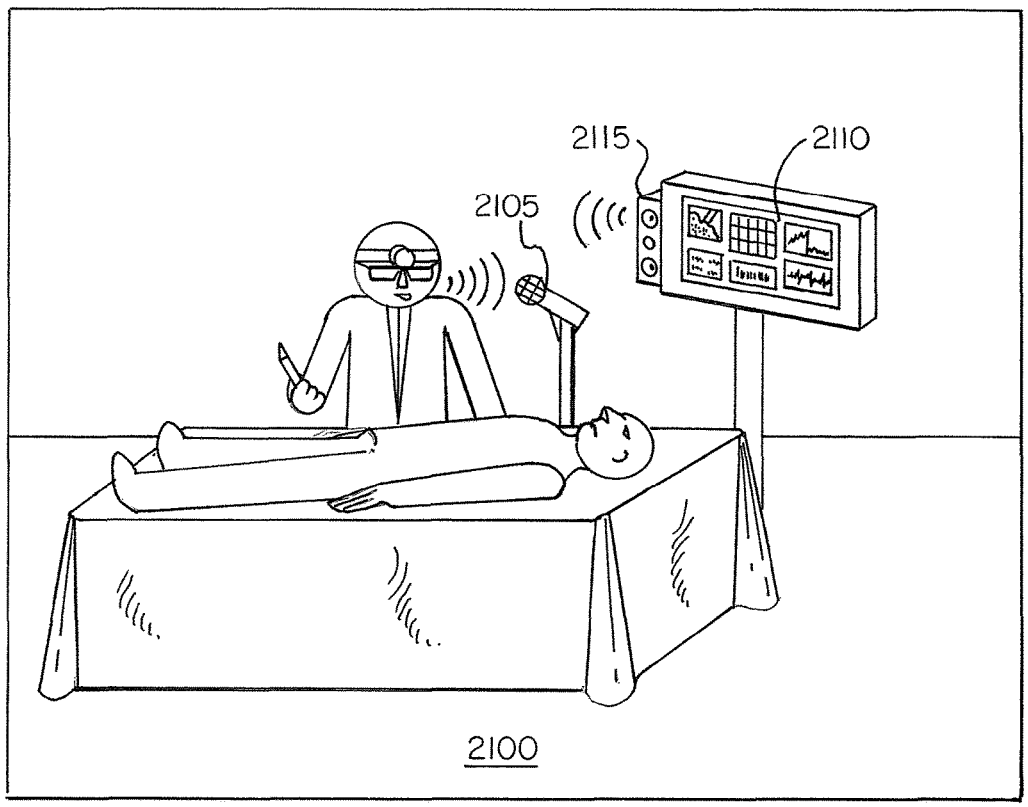
FIG. 14 illustrates a environment in which some embodiments of the invention may be used.

FIG. 14 illustrates a voice-controlled clinical information dashboard 2110 of some embodiments of the invention, such as a sterile environment 2100 (e.g., an operating room, an intensive care unit, etc.). FIG. 14 also shows an audio input device 2105 (e.g., a microphone) and an audio output device 2115 (e.g., a speaker or a set of speakers).

In this figure, a surgeon performs surgery on a patient in the environment 2100 while the voice-controlled clinical information dashboard 2110 displays clinical information (e.g., vital signs, lab results, etc.) in multiple windows (or "modalities"). The surgeon controls the voice-controlled clinical information dashboard 2110 (e.g., manipulates which information is displayed, inputs data, etc.) through voice commands. The voice commands are received by the audio input device 2105, which is communicatively coupled to a computer system (not shown) on which the clinical information dashboard 2110 runs.

In some embodiments, the audio output device 2115 outputs audio from the clinical dashboard 2110. This audio may include a spoken version of text and/or other data displayed by the clinical dashboard 2110. When used in a sterile environment, the voice-controlled clinical information dashboard 2110 eliminates the need for a user to compromise the sterile environment by "de-gowning" or "de-gloving" in order to control the dashboard through a traditional input mechanism (e.g., mice, keyboards, touch screens, scroll wheels, trackpads, etc.). The audio commands received by the system control and update the steps of the checklist in certain embodiments of the invention.

Figure 15:
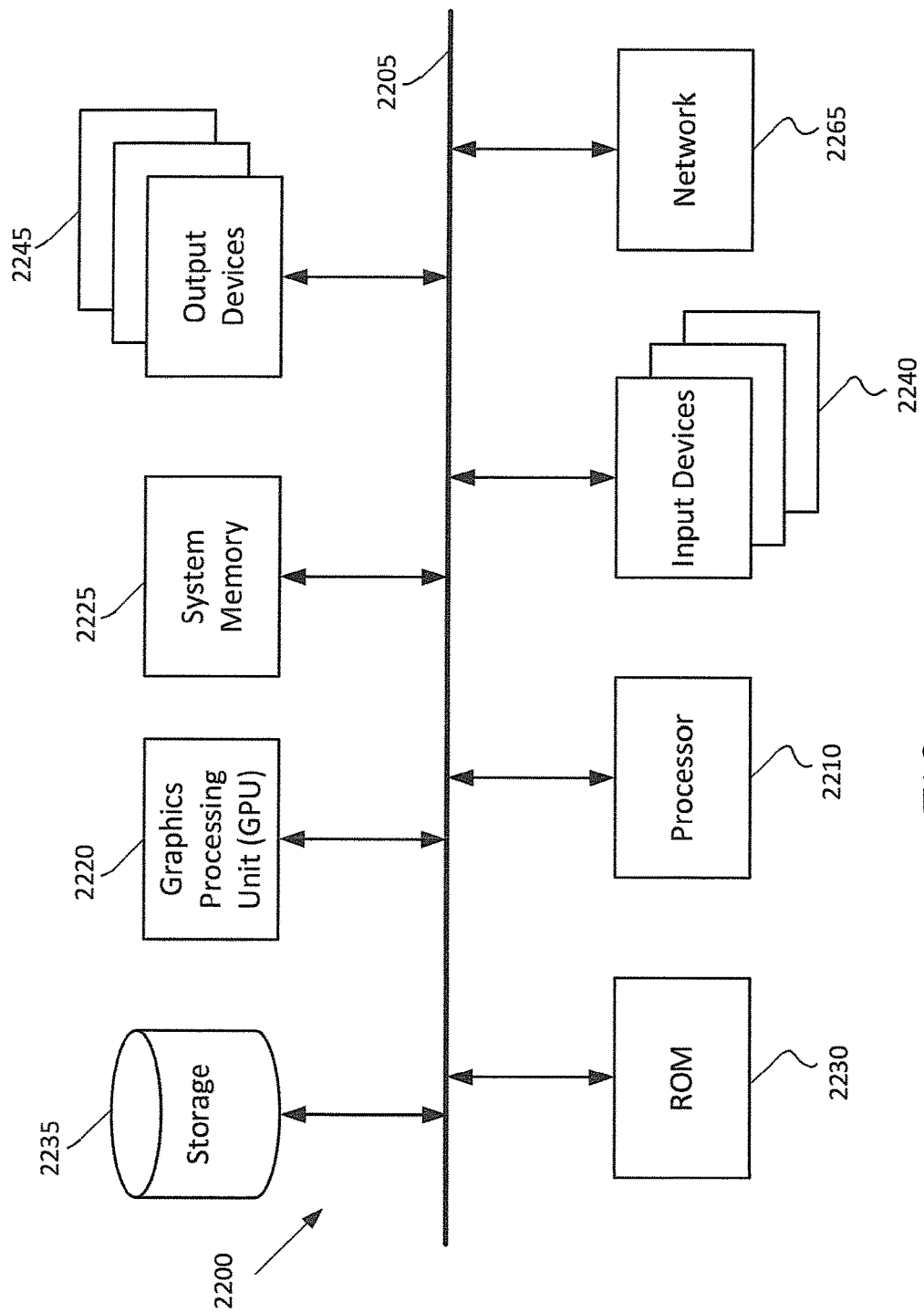
FIG. 15 illustrates a computer system in which some embodiments of the invention may be used.

FIG. 15 illustrates a computer system 2200 with which some embodiments of the invention are implemented. In some embodiments, the computer system 2200 includes various types of computer readable media and interfaces for various other types of computer readable media. Computer system 2200 includes a bus 2205, a processor 2210, a graphics processing unit ("GPU") 2220, a system memory 2225, a read-only memory ("ROM") 2230, a permanent storage device 2235, input devices 2240, and output devices 2245.

The bus 2205 collectively represents all system, peripheral, and chipset buses that communicatively connect the numerous internal devices of the computer system 2200. For instance, the bus 2205 communicatively connects the processor 2210 with the read-only memory 2230, the GPU 2220, the system memory 2225, and the permanent storage device 2235.

From these various memory units, the processor 2210 retrieves instructions to execute and data to process in order to execute the processes of the invention. Some instructions are passed to and executed by the GPU 2220. In some embodiments, the GPU 2220 can offload various computations or complement the image processing provided by the processor 2210.

The ROM 2230 stores static data and instructions that are used by the processor 2210 and other modules of the computer system. The permanent storage device 2235, on the other hand, is a read-and-write memory device. This device is a non-volatile memory unit that stores instructions and data even when the computer system 2200 is off. Some embodiments of the invention use a mass-storage device (such as a magnetic or optical disk and its corresponding disk drive) as the permanent storage device 2235.

Other embodiments use a removable storage device (such as a floppy disk, flash drive, or iOmega Zip® disk, and its corresponding disk drive) as the permanent storage device.

Like the permanent storage device 2235, the system memory 2225 is a read-and-write memory device. However, unlike storage device 2235, the system memory is a volatile read-and-write memory, such as a random access memory ("RAM"). The system memory stores some of the instructions and data that the processor needs at runtime. In some embodiments, the invention's processes are stored in the system memory 2225, the permanent storage device 2235, and/or the read-only memory 2230.

The bus 2205 also connects to the input and output devices 2240 and 2245. The input devices enable the user to communicate information and select commands to the computer system. In some embodiments, the input devices 2240 include alphanumeric keyboards and pointing devices (also called "cursor control devices"). In some embodiments, the input devices 2240 also include audio input devices (e.g., microphones, midi musical instruments, etc.). The output devices 2245 display images generated by the computer system. For instance, these devices display a GUI. The output devices include printers and display devices, such as cathode ray tubes ("CRT") or liquid crystal displays ("LCD").

In some embodiments, the computer system 2200 includes a set of hardware input/output ("I/O") ports (not shown) through which the input devices 2240 (e.g., a microphone) and output devices 2245 (e.g., a display device) supply and receive data. In some embodiments, this set of I/O ports includes an audio input port, such as a one-quarter or one-eighth inch port (or "jack"). In some embodiments, the set of I/O ports includes an audio output port, such as one or more one-quarter or one-eighth inch jacks. In some embodiments, one or both of these audio I/O ports include a wireless interface, such as radio frequency ("RF"), Bluetooth, or some other wireless interface. In some embodiments, the set of I/O ports includes a video output port (e.g., VGA, DVI, S-video etc.). Furthermore, the computer system 2200 may have other I/O ports not specifically enumerated or shown in the figure (e.g., USB ports, PS/2 ports, serial ports, etc.) for other input and/or output devices.

Finally, as shown in FIG. 22, bus 2205 also couples computer 2200 to a network 2265 through a network adapter (not shown). In this manner, the computer can be a part of a network of computers (such as a LAN, WAN, an intranet, or a network of networks, such as the Internet). For example, the computer 2200 may be coupled to a web server (through network 2265) so that a web browser executing on the computer 2200 can interact with the web server as a user interacts with a GUI that operates in the web browser.

Any or all components of computer system 2200 may be used in conjunction with the invention. For instance, in some embodiments, the rendering of the dashboards of some embodiments is performed by the GPU 2220 instead of the CPU 2210. Similarly, other image display functions can be offloaded to the GPU 2220 where they are executed before the results are passed back into memory or the processor 2210. However, a common limitation of the GPU 2220 is the number of instructions that the GPU 2220 is able to store and process at any given time. Therefore, some embodiments adapt instructions for implementing processes so that these processes fit onto the instruction buffer of the GPU 2220 for execution locally on the GPU 2220. Additionally, some GPUs 2220 do not have sufficient processing resources to execute the processes of some embodiments, and therefore the CPU 2210 executes the instructions. One of ordinary skill in the art would appreciate that any other system configuration may also be used in conjunction with the present invention.

As mentioned above, the computer system 2200 may include one or more of a variety of different computer-readable media. Some examples of such computer-readable media include tangible computer-readable media, such as RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, Iomega Zip® disks, read-only and recordable blu-ray discs, any other optical or magnetic media, and/or floppy disks.

FIG. 16 shows a surgical safety checklist provided by the World Health Organization (WHO). This surgical safety checklist and variations of such a checklist may be provided as automated checklists on the system of the present invention.

The present invention provides an updated and improved checklist over the checklist provided by the WHO as the present invention provides an automated checklist whereby clinical data is displayed on the checklist. Furthermore, the checklist can vary depending upon the surgical steps performed during the surgery and the status of the surgery.

While the invention has been specifically described in connection with certain specific embodiments thereof, it is to be understood that this is by way of illustration and not of limitation, and that various changes and modifications in form and details may be made thereto, and the scope of the appended claims should be construed as broadly as the prior art will permit.

The description of the invention is merely exemplary in nature, and, thus, variations that do not depart from the gist of the invention are intended to be within the scope of the invention. Such variations are not to be regarded as a departure from the spirit and scope of the invention.

What is claimed is:

1. A method for updating information on a display during a surgical procedure, the method comprising:
   collecting clinical data for a patient;
   providing a checklist on a display in a surgical operating room, the checklist including audio prompts corresponding to particular stages of a surgical procedure being performed in the surgical operating room;
   populating the checklist based on the clinical data of the patient, the checklist selected from a group of pre-stored checklists based upon the clinical data of the patient;
   receiving commands from a member of a surgical team through the audio prompts of the checklist, the received commands corresponding to a particular stage of the surgical procedure;
   automatically updating clinical data displayed on the display based upon the received commands, so that the clinical data displayed corresponds to a particular stage of the surgical procedure and to the received commands; and
   automatically updating a physical characteristic of the surgical operating room.

2. The method of claim 1, further comprising automatically updating the checklist based upon the commands received related to a particular stage of the surgical procedure.

3. The method of claim 2, further comprising automatically updating the steps of the surgical procedure based upon the updated checklist.

4. The method of claim 1, wherein the member of the surgical team is located within the surgical operating room.

5. The method of claim 1, wherein the commands received are transmitted to a database or to a system for the storage of patient information.

6. The method of claim 1, wherein a color of lighting in the surgical operating room is adjusted based upon a particular stage of the surgical procedure.

7. The method of claim 1, wherein the audio prompts include a first prompt in a first language and a second prompt in a second language, the first language being different than the second language.

8. The method of claim 1, wherein the audio prompts include a first prompt in a male voice and a second prompt in a female voice, and wherein the audio prompts can vary in volume intensity based upon the particular stage of the surgical procedure.

9. The method of claim 1, further comprising providing a rules database, the rules database providing a subset of pre-stored checklists based upon the clinical data of the patient.

10. The method of claim 1, wherein the clinical data is used to pre-populate the checklist prior to initiation of the surgical procedure.

11. The method of claim 1, further comprising tracking the particular stage of the surgical procedure via the checklist.

12. The method of claim 1, wherein the step of receiving commands from a member of a surgical team includes receiving voice commands from the member of the surgical team.

13. The method of claim 1, wherein the step of automatically updating the physical characteristic of the surgical operating room involves automatically updating a position of a component in the surgical operating room.

14. The method of claim 13, wherein the component includes a light and/or a display monitor.

15. A system for updating information on a display in a surgical operating room, the system comprising:
   a display configured to display clinical data for a patient;
   a checklist displayed on the display, the checklist including audio prompts corresponding to particular stages of a surgical procedure, the checklist being populated based on the clinical data of the patient, the checklist selected from a group of pre-stored checklists based upon the clinical data of the patient;
   software executing on a processor, the software tracking the particular stage of the surgical procedure via the checklist; and
   a receiver configured to receive commands from a member of a surgical team using the system, through the audio prompts of the checklist;
   wherein the software updates clinical data displayed on the display based upon the commands received from the member of the surgical team, so that the clinical data displayed corresponds to a particular stage of the surgical procedure and to the received commands; and
   wherein the software automatically updates a physical characteristic of the surgical operating room.

16. The system of claim 15, wherein the commands received are voice commands from the member of the surgical team.

17. The system of claim 15, wherein the checklist is updated based upon the commands received.

18. The system of claim 15, further comprising a surgical operating room;

wherein the display is located within the surgical operating room; and wherein the software adjusts lighting in the surgical operating room, based upon the particular stage of the surgical procedure.

19. The system of claim 15, wherein the color of a background of the display is updated based upon the particular stage of the surgical procedure.

20. The system of claim 15, wherein the display is divided into at least a first interface that displays the checklist and a second interface that displays the clinical data.

21. The system of claim 15, wherein the physical characteristic of the surgical operating room is a position of a light and/or a display monitor in the surgical operating room.

* * * * *